United States Patent [19]

Hughes et al.

[11] Patent Number: 5,032,592

[45] Date of Patent: * Jul. 16, 1991

[54] ALKENE, ALKYNE OR CYCLOALKYLENE DERIVATIVES

[75] Inventors: Leslie R. Hughes, Macclesfield; John Oldfield, Wilmslow; Howard Tucker, Macclesfield, all of England

[73] Assignee: Imperial Chemical Industries PLC, London, England

[*] Notice: The portion of the term of this patent subsequent to Oct. 10, 2006 has been disclaimed.

[21] Appl. No.: 358,433

[22] Filed: May 30, 1989

Related U.S. Application Data

[63] Continuation of Ser. No. 704,038, Feb. 21, 1985, Pat. No. 4,873,329.

[30] Foreign Application Priority Data

Mar. 7, 1984 [GB] United Kingdom ............... 8406000

[51] Int. Cl.$^5$ .................. A61K 31/53; A61K 31/185; C07D 473/00; C07C 255/00
[52] U.S. Cl. .................................... 514/256; 514/242; 514/258; 514/259; 514/261; 514/274; 514/297; 514/312; 514/347; 514/365; 514/383; 514/385; 514/438; 514/576; 544/265; 544/280; 544/283; 544/315; 544/318; 544/319; 546/103; 546/152; 546/153; 546/157; 546/172; 546/276; 546/280; 548/182; 548/186; 548/263; 548/337; 549/78; 549/79; 564/162; 564/221; 568/18; 568/27; 568/28; 568/308; 568/715; 568/775; 568/807
[58] Field of Search ............... 558/388, 413, 423; 514/242, 256, 258, 259, 261, 274, 297, 312, 347, 365, 383, 385, 438, 576; 544/265, 280, 315, 318, 319, 283; 546/103, 153, 157, 290, 301, 302, 152, 172, 276, 280; 548/182, 186, 263, 337; 549/78, 79; 568/308, 775, 32, 308, 18, 27, 28, 715, 807, 809, 812, 813; 564/162, 221

[56] References Cited

U.S. PATENT DOCUMENTS

| | | | |
|---|---|---|---|
| 3,979,471 | 9/1976 | Julia | 568/32 |
| 4,139,561 | 2/1979 | Onopchenko et al. | 260/575 |
| 4,191,775 | 3/1980 | Glen | 424/304 |
| 4,282,218 | 8/1981 | Glen et al. | 424/240 |
| 4,329,776 | 12/1980 | Glen et al. | 424/304 |
| 4,386,080 | 5/1983 | Crossley et al. | 564/125 |
| 4,507,140 | 3/1985 | Sugavanam | 71/76 |
| 4,532,341 | 7/1985 | Holmwood et al. | 549/559 |

FOREIGN PATENT DOCUMENTS 193303 9/1986 European Pat. Off.
128329 10/1977 Japan.

OTHER PUBLICATIONS

Reddy et al, Synthesis, Oct. 1980, pp. 815-817.

Primary Examiner—Cecilia Shen
Attorney, Agent, or Firm—Cushman, Darby & Cushman

[57] ABSTRACT

A compound of the formula

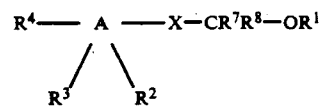

wherein X has the formula

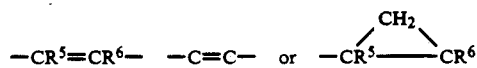

wherein ring A is phenyl, naphthyl or heterocyclic; wherein $R^1$ is hydrogen, alkyl, alkanoyl or aroyl; wherein $R^2$, $R^3$ and $R^4$, which may be the same or different, each is an electron withdrawing substituent selected from halogeno, nitro, cyano, trifluoromethyl, alkylthio, alkylsulphinyl, and alkylsulphonyl or each is hydrogen, alkyl, alkoxy or dialkylamino provided that when ring A is phenyl or naphthyl at least one of $R^2$, $R^3$ and $R^4$ is an electron-withdrawing substituent; wherein $R^5$ and $R^6$, which may be the same or different, each is hydrogen, halogeno or alkyl; wherein $R^7$ is alkyl or halogenoalkyl; and wherein $R^8$ is carbamoyl, alkyl, cycloalkyl, alkenyl, alkynyl, halogenoalkyl, halogenoalkenyl, halogenoalkynyl, alkanoyl, alkylcarbamoyl, dialkylcarbamoyl or aroyl; or wherein $R^8$ is alkyl or alkenyl which bears one or more substituents selected from cyano, carbamoyl, amino, hydroxy, alkanoyl, alkoxy, alkylthio, alkenylthio, alkylsulphinyl, alkenylsulphinyl, alkylsulphonyl, alkenylsulphonyl, alkanoylamino, alkoxycarbonylamino, alkylsulphonamido, alkylamino, dialkylamino, dialkylsulphamoyl, aroyl, aryl, arylthio, arylsulphinyl, arylsulphonyl, heterocyclylthio, heterocyclylsulphinyl and heterocyclylsulphonyl; or wherein $R^8$ has the formula

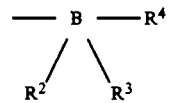

wherein ring B is phenyl, naphthyl or heterocyclyl and wherein $R^2$, $R^3$ and $R^4$ have any of the meanings stated above, provided that when $R^7$ is methyl $R^8$ is not also methyl.

5 Claims, No Drawings

ALKENE, ALKYNE OR CYCLOALKYLENE DERIVATIVES

This is a continuation of application Ser. No. 06/704,038, filed Feb. 21, 1985, now U.S. Pat. No. 4,873,329 issued Oct. 10, 1989.

This invention relates to novel alkene, alkyne or cycloalkylene derivatives which possess antiandrogenic properties.

Various 4-arylbut-3-en-2-ol derivatives of the general formula:

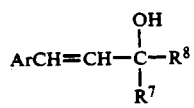

wherein Ar is a phenyl group bearing one or more electron-withdrawing substituents, are known, for a variety of purposes. For example, such compounds wherein $R^7$ is t-butyl and $R^8$ is imidazol-1-ylmethyl or 1,2,4-triazol-1-ylmethyl are known, from European Patent Specifications Nos 40345 and 52424 and other related specifications, as plant growth regulators or fungicides. When $R^7$ and $R^8$ are both methyl the compound wherein Ar is 3-nitrophenyl is known from United States Patent Specification No. 4139561, and the compound wherein Ar is 4-chlorophenyl is known from Synthesis, 1980, pages 815–816, in both cases the compounds being used as chemical intermediates. When $R^7$ is methyl, $R^8$ is carboxymethyl or ethoxycarbonylmethyl and Ar is 4-chlorophenyl, the compounds are described in Biochemistry, 1964, Volume 3, pages 1998 et seq., as potential (although inactive) inhibitors of cholesterol biosynthesis.

Various acylanilides of the general formula

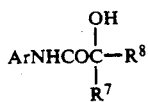

are known as antiandrogens. The compounds wherein $R^7$ and $R^8$ are both methyl and Ar is 4-nitro-3-trifluoromethylphenyl is known as hydroxyflutamide, and is believed to be the active metabolite of the commercially-available antiandrogen FLUTAMIDE. Other acylanilides which possess antiandrogenic activity are known from European Specifications Nos 2309, 2892 and 40932, and from Japanese Specification No. 52-128329.

According to the present invention there is provided a compound of the formula

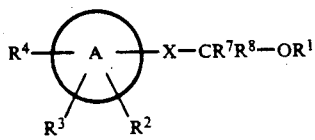

wherein X has the formula

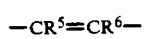

or

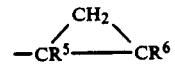

wherein ring A is phenyl, naphthyl or heterocyclic; wherein $R^1$ is hydrogen, alkyl or alkanoyl each of up to 6 carbon atoms or aroyl of up to 10 carbon atoms; wherein $R^2$, $R^3$ and $R^4$, which may be the same or different, each is an electron withdrawing substituent selected from halogeno, nitro, cyano and trifluoromethyl, and alkylthio, alkylsulphinyl and alkylsulphonyl each of up to 6 carbon atoms, or each is hydrogen or alkyl, alkoxy or dialkylamino each of up to 6 carbon atoms, provided that when ring A is phenyl or naphthyl at least one of $R^2$, $R^3$ and $R^4$ is an electron-withdrawing substituent; wherein $R^5$ and $R^6$, which may be the same or different, each is hydrogen, halogeno or alkyl of up to 6 carbon atoms, ; wherein $R^7$ is alkyl or halogenoalkyl each of up to 6 carbon atoms; and wherein $R^8$ is carbamoyl, alkyl, cycloalkyl, alkenyl, alkynyl, halogenoalkyl, halogenoalkenyl, halogenoalkynyl or alkanoyl each of up to 6 carbon atoms, or alkylcarbamoyl or dialkylcarbamoyl wherein each alkyl is of up to 6 carbon atoms, or aroyl of up to 10 carbon atoms; or wherein $R^8$ is alkyl or alkenyl each of up to 6 carbon atoms which bears one or more substituents selected from cyano, carbamoyl, amino and hydroxy, alkanoyl, alkoxy, alkylthio, alkenylthio, alkylsulphinyl, alkenylsulphinyl, alkylsulphonyl, alkenylsulphonyl, alkanoylamino, alkoxycarbonylamino and alkylsulphonamido each of up to 6 carbon atoms, alkylamino, dialkylamino and dialkylsulphamoyl wherein each alkyl is of up to 6 carbon atoms, aroyl, aryl, arylthio, arylsulphinyl and arylsulphonyl each of up to 10 carbon atoms and heterocyclylthio, heterocyclylsulphinyl and heterocyclylsulphonyl; or wherein $R^8$ has the formula

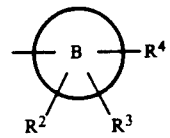

wherein ring B is phenyl, naphthyl or heterocyclyl and wherein $R^2$, $R^3$ and $R^4$ have any of the meanings stated above, provided that when $R^7$ is methyl $R^8$ is not also methyl.

It will be observed that a compound of the invention wherein X is other than ethynylene may exist in two geometrical isomeric forms depending upon the disposition of the various substituents about the olefinic or cycloalkyl bond —X—, and also that a compound of the invention wherein $R^7$ and $R^8$ are different one from the other possesses at least one asymmetric carbon atom, namely the carbon atom which bears the substituents $R^7$, $R^8$ and —$OR^1$, and it can therefore exist in racemic and optically-active forms. It is to be understood that this invention encompasses either geometric isomer in racemic form, and any optically-active form of the compound which possesses antiandrogenic activity, it being a matter of common general knowledge how a racemic compound may be resolved into its optically-active forms and how any antiandrogenic activity present in any of these forms may be determined.

A suitable value for ring A or B when it is heterocyclyl, or for the heterocyclyl group in $R^8$ when it is or contains heterocyclyl or heterocyclylthio-, sulphinyl- or sulphonyl-, is, for example, 5- or 6-membered saturated or unsaturated heterocyclic which contains one, two or three hetero atoms selected from oxygen, nitrogen and sulphur, which heterocyclic is a single ring or is fused to one or two benzo-rings or to another heterocyclic ring as defined above, and which heterocyclic is unsubstituted or bears substituents $R^2$, $R^3$ and $R^4$ as defined above, or when part of $R^8$ may also bear one or more hydroxy, mercapto or amino substituents.

Ring A when heterocyclic is preferably pyridyl, quinolyl or thienyl which is unsubstituted or bears one or two halogeno or cyano substituents, or one nitro substituent.

Ring B when heterocyclic is preferably pyridyl or thiazolyl which is unsubstituted or bears a halogeno or trifluoromethyl substituent, or is unsubstituted 1,3- dithian-2-yl.

When $R^8$ is alkyl or alkenyl bearing a heterocyclylthio, heterocyclylsulphinyl or heterocyclylsulphonyl substituent the heterocyclyl group is preferably pyridyl, quinolyl, pyrimidyl, thiazolyl, imidazolyl, triazolyl, purinyl, pyrazolopyrimidyl or acridyl which is unsubstituted or bears one or more substituents selected from halogeno, trifluoromethyl, hydroxy, mercapto and amino, and alkyl and alkoxy each of up to 6 carbon atoms.

A suitable value for $R^1$, $R^2$ $R^3$, $R^4$, $R^5$, $R^6$, $R^7$ or $R^8$ when it is alkyl is, for example, methyl, ethyl, n-propyl, isopropyl, n-butyl or n-hexyl.

A suitable value for $R^1$ or $R^8$ when it is alkanoyl, or for the alkanoyl substituent in $R^8$ when $R^8$ is alkyl or alkenyl substituted by alkanoyl is, for example, formyl, acetyl or propionyl.

A suitable value for $R^1$ or $R^8$ when it is aroyl, or for the aroyl substituent in $R^8$ when $R^8$ is alkyl or alkenyl substituted by aroyl, is, for example, benzoyl or p-toluoyl.

A suitable value for $R^2$, $R^3$, $R^4$, $R^5$ or $R^6$ when it is halogeno, or for the halogeno substituent in $R^8$ when $R^8$ is halogenoalkyl, halogenoalkenyl or halogenoalkynyl is, for example, fluoro, chloro or bromo.

A suitable value for $R^2$, $R^3$ or $R^4$ when it is alkoxy, or for the alkoxy substituent in $R^8$ when $R^8$ is alkyl or alkenyl substituted by alkoxy is, for example, methoxy or ethoxy.

A suitable value for $R^2$, $R^3$ or $R^4$ when it is alkylthio, alkylsulphinyl or alkylsulphonyl, or for the alkylthio, alkylsulphinyl or alkylsulphonyl substituent in $R^8$ when $R^8$ is alkyl or alkenyl substituted by alkylthio, alkylsulphinyl or alkylsulphonyl is, for example, methylthio, ethylthio, n-propylthio, methylsulphinyl, ethylsulphinyl, n-propylsulphinyl, methylsulphonyl, ethylsulphonyl or n-propylsulphonyl.

A suitable value for $R^2$, $R^3$ or $R^4$ when it is dialkylamino, or for the dialkylamino substituent in $R^8$ when $R^8$ is alkyl or alkenyl substituted by dialkylamino is, for example, dimethylamino or diethylamino.

A suitable value for $R^8$ when it is alkylcarbamoyl or dialkylcarbamoyl, is, for example, methylcarbamoyl or dimethylcarbamoyl.

A suitable value for $R^7$ or $R^8$ when it is halogenoalkyl is, for example, trifluoromethyl, pentafluoroethyl, heptafluoropropyl, chloromethyl or dichloromethyl.

A suitable value for $R^8$ when it is cycloalkyl, alkenyl or alkynyl is, for example, cyclopropyl, cyclopentyl, vinyl, allyl or ethynyl.

A suitable value for the alkoxycarbonylamino, alkanoylamino, alkylsulphonamido, alkylamino or dialkylsulphamoyl substituent in $R^8$ when $R^8$ is alkyl or alkenyl which bears such a substituent is, for example, methoxycarbonylamino, ethoxycarbonylamino, acetamido, methylsulphonamido, methylamino, ethylamino or dimethylsulphamoyl.

A suitable value for the aryl, arylthio, arylsulphinyl or arylsulphonyl substituent in $R^8$ when $R^8$ is alkyl or alkenyl which bears such a substituent is, for example, phenyl, tolyl, fluorophenyl, chlorophenyl, nitrophenyl, methylthiophenyl, methylsulphonylphenyl carbamoylphenyl, acetamidophenyl or dimethylaminophenyl, or the corresponding phenylthio, phenylsulphinyl, phenylsulphonyl or substituted phenylthio, phenylsulphinyl or phenylsulphonyl.

A suitable value for the alkenylthio, alkenylsulphinyl or alkenylsulphonyl substituent in $R^8$ when $R^8$ is alkyl or alkenyl which bears such a substituent is, for example, allylthio, allylsulphinyl or allylsulphonyl.

A preferred compound of the invention has the formula stated above wherein X is $-CR^5=CR^6-$, wherein ring A is phenyl, wherein one or two (the same or different) of $R^2$, $R^3$ and $R^4$ are fluoro, chloro, cyano, trifluoromethyl or nitro, the others of $R^2$, $R^3$ and $R^4$ being hydrogen, wherein $R^1$, $R^5$ and $R^6$ are all hydrogen, wherein $R^7$ is trifluoromethyl, pentafluoroethyl, heptafluoropropyl, chloromethyl or dichloromethyl, wherein $R^8$ is methyl, ethyl, n-propyl, isopropyl, n-butyl, cyclopropyl, trifluoromethyl, chloromethyl, dichloromethyl, ethynyl, chloroethynyl, acetyl or propionyl or is methylene ($-CH_2-$) substituted by cyano, hydroxy, carbamoyl, formyl, acetyl, alkylthio, alkenylthio, alkylsulphonyl or alkenylsulphenyl each of up to 6 carbon atoms, phenylthio or phenylsulphonyl which itself is unsubstituted or bears a fluoro, chloro, nitro, carbamoyl, acetamido, methylthio or methylsulphonyl substituent, pyridyl, quinolyl, pyrimidinyl, purinyl, pyrazolopyrimidinyl, thiazolyl, imidazolyl or triazolyl any of which is unsubstituted or bears a hydroxy, mercapto, amino, chloro, trifluoromethyl or methyl substituent, and wherein the $-CR^5=CR^6-$ group is in the trans- configuration.

A particularly preferred compound of the invention has the formula stated above wherein X is trans- $-CH=CH-$, wherein ring A is 3,4-dichlorophenyl, 3-chloro-4-cyanophenyl, 3-chloro-4-fluorophenyl, 4-chloro-3-trifluoromethylphenyl, 4-cyanophenyl, 4-cyano-3-fluorophenyl, 4-cyano-3-trifluoromethylphenyl or 4-fluoro-3- trifluoromethylphenyl, wherein $R^1$ is hydrogen, wherein $R^7$ is trifluoromethyl and wherein $R^8$ is ethyl, ethynyl, cyanomethyl, 1-cyanoethyl, acetyl, methylsulphonylphenyl, p-methylsulphonyl-phenylsulphonylmethyl or pyrid-2-ylsulphonyl, or has the formula $-CH_2SR^9$ wherein $R^9$ is m-methylthiophenyl, pyrid-4-yl, pyrimid-2-yl, 4,6-dimethylpyrimid-2-yl, purin-6-yl, 1H-pyrazolo[3,4-d]pyrimidin-4-yl, imidazol-2-yl, 1-methylimidazol-2-yl, 7-chloroquinolin-4-yl or 7-trifluoromethylquinolin-4-yl.

Specific compounds of the invention are hereinafter described in the Examples. Of these, preferred compounds by virtue of their high level of antiandrogenic activity are:

5-(3,4-dichlorophenyl)-3-hydroxy-3-trifluoromethyl-pent-trans-4-en-2-one;

5-(3,4-dichlorophenyl)- and 5-(4-cyano-3-trifluoromethylphenyl)-3-trifluoromethylpent-trans-4-en-1-yn-3-ol;

5-(4-cyanophenyl)- and 5-(4-cyano-3-trifluoromethylphenyl)-3-hydroxy-3-trifluoromethylpent-trans-4-enenitrile;

4-(3-chloro-4-fluorophenyl-, 4-cyanophenyl-, 4-cyano-3-trifluoromethylphenyl-, 4-chloro-3- trifluoromethylphenyl and 4-fluoro-3-trifluoromethyl-phenyl)-1-methylsulphonyl-2-trifluoromethylbut-trans3-en-2-ol;

5-(3,4-dichlorophenyl)-3-hydroxy-2-methyl-3-trifluoromethylpent-trans-4-enenitrile;

4-(3,4-dichlorophenyl)-1-(pyrid-4-ylthio)-2-trifluoromethylbut-trans-3-en-2-ol;

4-(3,4-dichlorophenyl)-1-(pyrimidin-2-ylthio)-2-trifluoromethylbut-trans-3-en-2-ol;

4-(3,4-dichlorophenyl)-1-(pyrid-2-ylsulphonyl)-2-trifluoromethylbut-trans-3-en-2-ol;

4-(4-cyano-3-trifluoromethylphenyl)-1-(7-chloroquinolin-4-ylthio)-, 1-(7-trifluoromethylquinolin-4-ylthio)-, 1-(pyrimidin-2-ylthio)-, 1-(4,6-dimethylpyrimidin-2-ylthio)-, 1-(purin-6-ylthio)-, 1-(1H-pyrazolo[3,4-d]pyrimidin-4-ylthio)-1-(imidazol-2-ylthio)- and 1-(1-methylimidazol-2-ylthio)-2-trifluoromethylbut-trans-3-en-2-ol;

5-(3,4-dichlorophenyl)- and 5-(4-cyano-3-trifluoromethylphenyl)-3-trifluoromethylpent-trans-3-en-2-ol;

4-(3-chloro-4-cyanophenyl)-1-(p-methylsulphonylphenyl)thio-2-trifluoromethylbut-trans-3-en-2-ol; and 4(3-chloro-4-cyanophenyl)-1-(p-methylsulphonylphenylsulphonyl)-2-trifluoromethylbut-trans-3-en-2-ol.

A compound of the invention may be manufactured by any chemical process known to be suitable for the manufacture of chemically-analogous compounds.

One process for the manufacture of an alkene of the invention wherein $R^1$ is hydroxy and X is $-CR^5=CR^6-$ comprises the reaction of a compound of the formula:

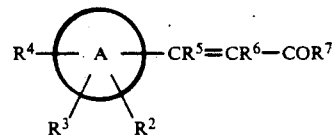

wherein A, $R^2$, $R^3$, $R^4$, $R^5$, $R^6$ and $R^7$ have the meanings stated above, with an organometallic compound of the formula $R^8-M$, wherein $R^8$ has the meaning stated above and M is a metallic group.

M may be, for example, lithium, and the reaction is preferably carried out in an inert diluent or solvent, for example tetrahydrofuran, at a reduced temperature, for example at $-70°$ C. to $-80°$ C.

The starting material for the abovementioned reaction may be obtained by the reaction of an aldehyde or ketone of the formula:

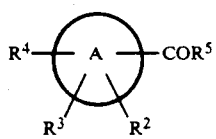

wherein A, $R^2$, $R^3$, $R^4$ and $R^5$ have the meanings state above, with a compound of the formula $$R^6CH_2COR^7 \text{ or } (Ph)_3P=CR^6COR^7 \text{ or } (EtO)_2POCHR^6-R^7 \overset{NMe}{\underset{\|}{C}}$$

wherein $R^6$ and $R^7$ have the meanings stated above.

An alternative process for the manufacture of an alkene of the invention wherein $R^1$ is hydroxy, X is $-CR^5=CR^6-$, and $R^8$ has the formula comprises the reaction of an epoxide of the formula:

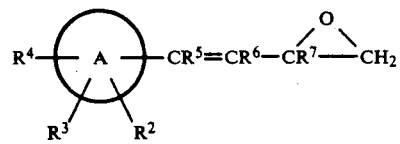

wherein A, $R^2$, $R^3$, $R^4$, $R^5$, $R^6$ and $R^7$ have the meanings stated above, with a compound of the formula $R^9-H$, wherein $R^9$ is such that $-CH_2R^9$ has the meaning stated above for $R^8$.

The abovementioned reaction is particularly suitable for the manufacture of an alkene of the invention wherein $R^9-H$ contains a reactive thiol group, or wherein the $-H$ atom is otherwise reactive. The reaction is conveniently carried out at laboratory temperature in an inert diluent or solvent, for example tetrahydrofuran or diethyl ether.

The epoxide starting material may be obtained by the reaction of a compound of the formula:

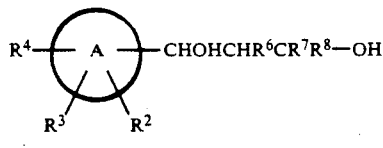

(the preparation of which is described above) with trimethylsulphox-onium iodide in the presence of a base, for example butyl-lithium or, under phase transfer conditions, an alkali metal hydroxide.

An alternative process for the manufacture of an alkene of the invention wherein $R^1$ and $R^5$ are both hydrogen and X is $-CH=CR^6-$ comprises the dehydration of a compound of the formula

wherein A, $R^2$, $R^3$, $R^4$, $R^6$, $R^7$ and $R^8$ have the meanings stated above.

The dehydration may be carried out under acidic conditions, for example by heating with p-toluenesulphonic acid.

The starting material may be obtained by reacting a compound of the formula

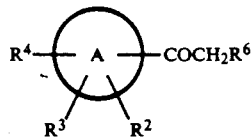

with a compound of the formula $R^7COR^8$, followed by the reduction of the compound of the formula

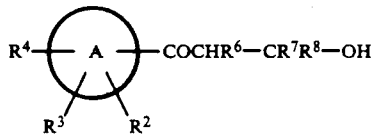

thus obtained.

An alternative process for the manufacture of an alkene of the invention wherein $R^1$ is hydroxy and X is $-CR^5=CR^6-$ comprises the reaction of a compound of the formula

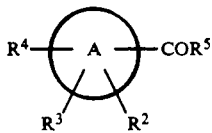

wherein A, $R^2$, $R^3$, $R^4$ and $R^5$ have the meanings stated above, with a compound of the formula $$R^7COR^8$$

wherein $R^7$ and $R^8$ have the meanings stated above.

This reaction may be carried out in the presence of a phosphonium bromide, for example methyltriphenylphosphonium bromide, and an alkyl-metal compound, for example s-butyl-lithium, at a low temperature in an inert diluent or solvent.

A process for the manufacture of a cycloalkylene alkylene derivative of the invention wherein X is

comprises the reaction of a compound of the formula

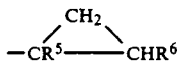

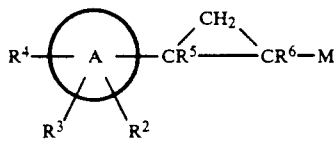

wherein A, $R^2$, $R^3$, $R^4$, $R^5$, $R^6$ and M have the meanings stated above, with a compound of the formula $$R^7COR^8$$

wherein $R^7$ and $R^8$ have the meanings stated above.

This reaction may be carried out at a low temperature in an inert diluent or solvent. M is preferably lithium.

A process for the manufacture of an alkyne of the invention wherein X is $-C\equiv C-$ comprises the reaction of a compound of the formula

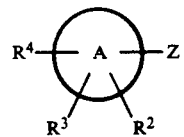

wherein A, $R^1$, $R^2$, $R^3$ and $R^4$ have the meanings stated above and wherein Z is a displaceable group, with a compound of the formula

wherein $R^1$, $R^7$ and $R^8$ have the meanings stated above.
A suitable value for Z is, for example, an iodo group.

A compound of the invention wherein X is $-C\equiv C-$ may be reduced to the corresponding compound of the invention wherein X is $-CH=CH-$. Conventional conditions for the reduction may be chosen so that either the cis- or trans- alkene is obtained.

Various interconversions of compounds of the invention wherein $R^8$ has different meanings are possible. Thus, for example (i) a compound wherein $R^8$ bears an amino substituent may be acylated to give the corresponding compound wherein $R^8$ bears an alkanoylamino, alkoxycarbonylamino or alkylsulphonamido substituent;

(ii) a compound wherein $R^8$ is alkyl containing an alkylthio and an alkylsulphinyl substituent on the same carbon atom may be converted to the corresponding compound wherein said carbon atom is a carbonyl group;

(iii) a compound wherein $R^8$ is alkanoyl or is alkyl substituted by alkanoyl may be reduced to the corresponding compound wherein $R^8$ is hydroxyalkyl; or (iv) a compound wherein $R^8$ is alkynyl may be converted to the corresponding compound wherein $R^8$ is alkanoyl by hydration by conventional means, for example with mercuric oxide.

A compound of the invention wherein $R^1$ is alkyl may be prepared by the alkylation of the corresponding compound wherein $R^1$ is hydrogen.

A compound of the invention wherein $R^1$ is alkanoyl or aroyl may be prepared by the acylation of the corresponding compound wherein $R^1$ is hydrogen.

A compound of the invention wherein one or more of $R^2$, $R^3$, $R^4$ and a substituent in $R^8$ is alkylsulphinyl or alkylsulphonyl, or a substituent in $R^8$ is alkenylsulphinyl, arylsulphinyl, alkenylsulphonyl, arylsulphonyl, heterocyclylsulphinyl or heterocyclylsulphonyl, may be prepared by the oxidation of the corresponding compound wherein one or more of $R^2$, $R^3$, $R^4$ and a substituent in $R^8$ is alkylthio, alkenylthio, arylthio or heterocyclylthio, respectively. The oxidising agent and conditions used will determine whether a sulphinyl or a sulphonyl compound is obtained. Thus, oxidation with sodium metaperiodate in methanol solution at or below laboratory temperature will generally convert a thio compound into the corresponding sulphinyl compound; and oxidation with hydrogen peroxide in acetic acid solution or with a persulphate in aqueous solution at or above laboratory temperature, will generally convert a thio compound into the corresponding sulphonyl compound, although this reaction occasionally stops at the sulphinyl stage.

As stated above, a compound of the invention possesses antiandrogenic properties as demonstrated by its ability to decrease the weight of the seminal vesicles of a castrated male rat when administered concurrently with testosterone propionate. A compound of the invention may therefore be used in the treatment of, for example, malignant or benign prostatic disease or of androgen dependent disease conditions, such as acne, hirsutism or seborrhoea, in warm-blooded vertebrates including man. It may also be used to improve ovulation in a domestic animal.

At a dose of a compound of the invention which produces antiandrogenic activity in rats no symptom of toxicity is apparent.

The compound of the invention may be administered to a warm-blooded animal in the form of a pharmaceutical or veterinary composition which comprises the compound in association with a pharmaceutically-acceptable diluent or carrier.

The composition may be in a form suitable for oral dosage, as a tablet, capsule, aqueous or oily solution or suspension, or emulsion. It may alternatively be in the form of a sterile solution or suspension suitable for parenteral administration, or be in the form of an ointment or lotion for topical administration, or be in the form of a suppository.

The composition may additionally contain one or more drugs selected from anti-oestrogens, for example tamoxifen; aromatase inhibitors, for example testolactone or aminoglutethimide; progestins, for example medroxyprogesterone acetate; inhibitors of gonadotrophin secretion, for example danazol; LH-RH analogues, for example buserelin; cytotoxic agents, for example cyclo-phosphamide; antibiotics, for example penicillin or oxytetracyclin; and anti-inflammatory agents, for example, especially for topical use, fluocinolone acetonide.

The compound of the invention will normally be administered to a warm-blooded animal at a dose of between 0.1 mg. and 125 mg. per kg. bodyweight.

The invention is illustrated but not limited by the following Examples:

EXAMPLE 1 n-Butyl-lithium (2.1 ml. of a 1.6 molar solution in hexane) was added dropwise to a stirred solution of dimethyl sulphone (0.31 g.) in tetrahydrofuran (50 ml.) which was cooled to $-78°$ C., and the mixture was stirred for 1 hour. A solution of 1,1,1-trifluoro-4-(3,4-dichlorophenyl)but-trans-3-ene-2-one (0.75 g.) in tetrahydrofuran (25 ml.) was added dropwise, the mixture was stirred at $-78°$ C. for 20 minutes, and a mixture of methanol (10 ml.) and saturated aqueous ammonium chloride solution (20 ml.) was added. The mixture was allowed to warm up to laboratory temperature and poured into water, and the mixture was extracted with ethyl acetate. The extract was washed with water and then with saturated aqueous sodium chloride solution, dried over magnesium sulphate and evaporated to dryness under reduced pressure. The residue was purified by chromatography on a silica gel column using methylene chloride as eluant, and there was thus obtained 4-(3,4-dichlorophenyl)-1-methylsulphonyl-2-trifluoromethylbut-trans-3-en-2-ol, m.p. 110° C.

The 1,1,1-trifluoro-4-(3,4-dichlorophenyl)but-trans-3-ene-2-one used as starting material was obtained as follows:

A solution of 3,4-dichlorobenzaldehyde (10 g.) in ethanol (50 ml.), and then 1,1,1-trifluoroacetone (6.5 ml.), were successively added to a stirred suspension of freshly ground lithium hydroxide monohydrate (1.0 g.) in ethanol (100 ml.), the trifluoroacetone being added by injection below the surface of the reaction mixture, and the mixture was stirred for 1 hour and then poured into water (600 ml.). The mixture was extracted with ethyl acetate and the extract was washed with aqueous 2N-hydrochloric acid and then saturated aqueous sodium chloride solution, dried over magnesium sulphate and evaporated to dryness under reduced pressure. The residue was purified by chromatography on a silica gel column using a 7:3 v/v mixture of petroleum ether (b.p. 60°-80° C.) and methylene chloride as eluant. There was thus obtained 1,1,1-trifluoro-4-(3,4-dichlorophenyl)but-trans-3-en-2-one, m.p. 81° C.

EXAMPLE 2

The process described in Example 1 was repeated using the appropriate organometallic compound and the appropriate 4-arylbut-trans-3-en-2-one as starting materials, and there were thus obtained the compounds described in the following tables:

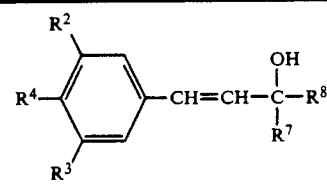

| $R^2$ | $R^3$ | $R^4$ | $R^7$ | $R^8$ | m.p. (°C.) | Note |
|---|---|---|---|---|---|---|
| H | H | F | $CF_3$ | $CH_2SO_2CH_3$ | 116 | |
| H | H | CN | $CF_3$ | $CH_2SO_2CH_3$ | 156 | |
| H | $CF_3$ | F | $CF_3$ | $CH_2SO_2CH_3$ | 126 | |
| H | Cl | F | $CF_3$ | $CH_2SO_2CH_3$ | 95 | |
| H | H | $NO_2$ | $CF_3$ | $CH_2SO_2CH_3$ | (oil) | |
| H | $CF_3$ | Cl | $CF_3$ | $CH_2SO_2CH_3$ | 136 | |
| Cl | Cl | H | $CF_3$ | $CH_2SO_2CH_3$ | 132 | |
| H | $CF_3$ | H | $CF_3$ | $CH_2SO_2CH_3$ | 89–92 | |
| H | $CF_3$ | CN | $CF_3$ | $CH_2SO_2CH_3$ | 173–174 | 9 |
| H | Cl | CN | $CF_3$ | $CH_2SO_2CH_3$ | 115 | 9 |
| H | $CH_3O$ | CN | $CF_3$ | $CH_2SO_2CH_3$ | 134–136 | |
| H | CN | H | $CF_3$ | $CH_2SO_2CH_3$ | 150–154 | |
| H | F | CN | $CF_3$ | $CH_2SO_2CH_3$ | 150–151 | 9 |
| H | $CF_3$ | $NO_2$ | $CF_3$ | $CH_2SO_2CH_3$ | 121–122 | |
| H | Cl | Cl | $C_2F_5$ | $CH_2SO_2CH_3$ | 94–95 | 6 |
| H | Cl | Cl | $C_3F_7$ | $CH_2SO_2CH_3$ | 104–105 | 6 |
| H | $CF_3$ | CN | $CH_3$ | $CH_2SO_2CH_3$ | 110–111 | 6, 9 |

-continued

| | | | | | | |
|---|---|---|---|---|---|---|
| H | Cl | Cl | CH₂Cl | CH₂SO₂CH₃ | 113 | 3 |
| H | H | CN | CF₃ | CH₂SO₂C₂H₅ | 138 | |
| H | Cl | CN | CF₃ | CH₂SO₂C₂H₅ | 125 | 9 |
| H | CF₃ | CN | CF₃ | CH₂SO₂C₂H₅ | 163 | 9 |
| H | Cl | F | CF₃ | CH₂SO₂C₂H₅ | 88 | |
| H | Cl | Cl | CF₃ | CH₂SO₂N(CH₃)₂ | 106 | 1 |
| H | CF₃ | Cl | CF₃ | CH₂SO₂N(CH₃)₂ | 102 | 1 |
| H | CF₃ | CN | CF₃ | CH₂SO₂N(CH₃)₂ | 160 | 1, 9 |
| H | Cl | Cl | CF₃ | CH₂SO₂C₆H₅ | 102 | |
| H | CF₃ | CN | CF₃ | CH₂SO₂C₆H₅ | 106 | 9 |
| H | Cl | CN | CF₃ | CH₂SO₂(4-fluorophenyl) | (oil) | 9 |
| H | CF₃ | CN | CF₃ | CH₂SO₂(4-fluorophenyl) | 138 | 9 |
| H | Cl | Cl | CF₃ | CH₂CN | 116 | 1 |
| H | NO₂ | Cl | CF₃ | CH₂CN | 111 | 1 |
| H | H | CN | CF₃ | CH₂CN | (oil) | 1 |
| H | Cl | F | CF₃ | CH₂CN | 86 | 1 |
| H | CF₃ | Cl | CF₃ | CH₂CN | (oil) | 1 |
| H | CF₃ | NO₂ | CF₂ | CH₂CN | 99–101 | 1 |
| H | CF₃ | CN | CF₃ | CH₂CN | 117–118 | 1, 9 |
| H | CN | Cl | CF₃ | CH₂CN | (oil) | 1 |
| H | CF₃ | F | CF₃ | CH₂CN | (oil) | 1 |
| H | Cl | Cl | C₂F₅ | CH₂CN | (oil) | 1,6 |
| H | Cl | Cl | C₃F₇ | CH₂CN | (oil) | 1,6 |
| H | Cl | Cl | CH₃ | CH₂CN | (oil) | 1,6 |
| H | Cl | Cl | CHCl₂ | CH₂CN | 77 | 1,4 |
| H | Cl | Cl | CF₃ | CH(CH₃)CN | 86 | 1(Isomer A) |
| H | Cl | Cl | CF₃ | CH(CH₃)CN | 129 | 1(Isomer B) |
| H | H | CN | CF₃ | CH(CH₃)CN | (oil) | 1(Isomer A) |
| H | H | CN | CF₃ | CH(CH₃)CN | 112 | 1(Isomer B) |
| H | CF₃ | Cl | CF₃ | CH(CH₃)CN | 97 | 1(Isomer A) |
| H | CF₃ | Cl | CF₃ | CH(CH₃)CN | 78 | 1(Isomer B) |
| H | Cl | F | CF₃ | CH(CH₃)CN | 79 | 1(Isomer A) |
| H | Cl | F | CF₃ | CH(CH₃)CN | 84 | 1(Isomer B) |
| H | CF₃ | CN | CF₃ | CH(CH₃)CN | (oil) | 1,9 (Isomer A) |
| H | CF₃ | CN | CF₃ | CH(CH₃)CN | (oil) | 1, 9 (Isomer B) |
| H | Cl | Cl | CF₃ | CH(C₂H₅)CN | 88 | 1(Isomer A) |
| H | Cl | Cl | CF₃ | CH(C₂H₅)CN | 108 | 1(Isomer B) |
| H | Cl | Cl | CF₃ | C(CH₃)₂CN | (oil) | 1 |
| H | Cl | Cl | CF₃ | ethynyl | 41 | 5 |
| H | H | CN | CF₃ | ethynyl | 83 | 5 |
| H | CF₃ | F | CF₃ | ethynyl | (oil) | 5 |
| H | F | F | CF₃ | ethynyl | (oil) | 5 |
| H | Cl | F | CF₃ | ethynyl | (oil) | 5 |
| H | CF₃ | Cl | CF₃ | ethynyl | (oil) | 5 |
| H | CF₃ | NO₂ | CF₃ | ethynyl | (oil) | 5 |
| Cl | Cl | H | CF₃ | ethynyl | (oil) | 5 |
| H | CF₃ | H | CF₃ | ethynyl | (oil) | 5 |
| H | CF₃ | CN | CF₃ | ethynyl | 121–123 | 5, 9 |
| H | CN | H | CF₃ | ethynyl | (oil) | 5 |
| H | CN | Cl | CF₃ | ethynyl | (oil) | 5 |
| H | Cl | Cl | C₂F₅ | ethynyl | (oil) | 5,6 |
| H | CN | H | CH₃ | ethynyl | (oil) | 5,6 |
| H | CF₃ | CN | CH₃ | ethynyl | (oil) | 5,6 |
| H | Cl | Cl | CH₂Cl | ethynyl | (oil) | 3,5 |
| H | Cl | Cl | CHCl₂ | ethynyl | (oil) | 4,5 |
| H | Cl | Cl | CF₃ | chloroethynyl | 78 | |
| H | Cl | Cl | CF₃ | methyl | (oil) | |
| H | Cl | Cl | CF₃ | n-butyl | (oil) | |
| H | Cl | Cl | CF₃ | cyclopropyl | 48–50 | |
| H | Cl | Cl | CF₃ | allyl | (oil) | |
| H | Cl | Cl | CF₃ | CHCl₂ | 49 | 1 |
| H | Cl | Cl | CF₃ | CF=CF₂ | 60 | 2 |
| H | Cl | Cl | CF₃ | CH₂COCH₃ | 91 | 1 |
| H | Cl | Cl | CF₃ | CH₂CONH₂ | 126 | 8 |
| H | H | CN | CF₃ | C(OCH₃)=CH₂ | (oil) | 7 |
| H | Cl | Cl | CF₃ | C(SC₆H₅):CH₂ | (oil) | |
| H | Cl | Cl | CF₃ | CH(SCH₃)SOCH₃ | 75 | |
| H | Cl | Cl | CF₃ | C(C₂H₅)(SCH₃)SOCH₃ | (oil) | |
| H | Cl | Cl | CF₃ | 1,3-dithian-2-yl | 110 | |
| H | Cl | Cl | CF₃ | 6-fluoropyrid-3-yl | 92 | 2 |
| H | Cl | Cl | CF₃ | 4-trifluoromethyl-thiazol-2-yl | 81 | |
| H | Cl | Cl | CF₃ | 4-dimethylaminophenyl | 130 | 2 |
| H | Cl | Cl | CF₃ | 4-cyanophenyl | (oil) | |
| H | Cl | Cl | CH₃ | 4-cyanophenyl | 75 | 6 |

Note 1 Lithium diisopropylamide was used in place of n-butyl-lithium.
Note 2 n-Butyl-lithium was reacted with a compound of the formula $R^8$—Br in place of $R^8$—H.
Note 3 The butenone starting material was obtained by the reaction of 3,4-dichlorobenzaldehyde (1.75 g.) and -continued (3-chloroacetonylidene)triphenylphosphorane (1.76 g.) in toluene (25 ml.) solution at 80° C. for 3 hours, evaporation to dryness, extraction of the residue with cyclohexane and purification of the extracted product by chromatography on a silica gel column using a 7:3 v/v mixture of petroleum ether (b.p. 60–80° C.) and methylene chloride. 1-Chloro-4-(3,4-dichlorophenyl)but-trans-3-en-2-one has m.p. 72° C.

Note 4 The butenone starting material was obtained by the reaction of 3,4-dichlorobenzaldehyde (0.34 g.) and (3,3-dichloroacetonylidene)triphenylphosphorane (0.15 g.) at 135° C. under an atmosphere of argon for 2 hours, followed by isolation and chromatographic purification by a similar procedure to that described under Note 3. 1,1-Dichloro-4-(3,4-dichlorophenyl)but-trans-3-en-2-one has m.p. 114° C.

Note 5 The butenone was reacted with trimethylsilyl-acetylene and the trimethylsilyl protecting group was removed by stirring the reaction product with tetra-n-butylammonium fluoride in tetrahydrofuran solution at laboratory temperature.

Note 6 The appropriate ketone (acetone, methyl pentafluoroethyl ketone or methyl heptafluoropropyl ketone) was used in place of trifluoroacetone in the preparation of the starting materials.

Note 7 t-Butyl-lithium was used in place of n-butyl-lithium.

Note 8 The butenone was reacted with N,N-bis-trimethyl-silylacetamide, the trimethylsilyl protecting groups being removed during the work-up of the reaction product without a specific deprotection step being necessary.

Note 9 The butenone starting material was obtained by the reaction of the appropriate aldehyde with diethyl 3,3,3-trifluoro-2-methyliminopropylphosphonate by the method described in Tetrahedron Letters (1983), page 4229. 4-(4-Cyano-3-trifluoromethylphenyl)-1,1,1-trifluorobut-3-en-2-one has m.p. 119–121° C., 4-(4-cyano-3-fluorophenyl)-1,1,1-trifluorobut-3-en-2-one has m.p. 69–70° C., and 4-(3-chloro-4-cyanophenyl)-1,1,1-trifluorobut-3-en-2-one has m.p. 102–104° C.

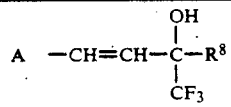

| $R^2$ | $R^4$ | $R^7$ | $R^8$ | m.p. (°C.) | Note |
|---|---|---|---|---|---|
| F | F | $CF_3$ | $CH_2SO_2CH_3$ | 145 | |
| F | F | $CF_3$ | ethynyl | (oil) | 5 |

Note 5 The butenone was reacted with trimethylsilylacetylene and the trimethylsilyl protecting group was removed by stirring the reaction product with tetra-n-butylammonium fluoride in tetrahydrofuran solution at laboratory temperature.

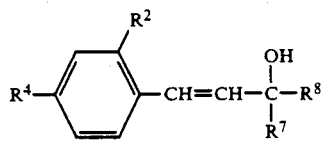

| A | $R^8$ | m.p. (°C.) | Note |
|---|---|---|---|
| pyrid-3-yl | $CH_2CN$ | (oil) | 1 |
| pyrid-4-yl | $CH_2CN$ | (oil) | 1 |
| 6-chloropyrid-3-yl | $CH_2CN$ | (oil) | 1 |
| quinolin-3-yl | $CH_2CN$ | (oil) | 1 |
| 5-bromothien-2-yl | $CH_2CN$ | (oil) | 1 |
| pyrid-4-yl | $CH_2SO_2CH_3$ | (oil) | |
| 6-chloropyrid-3-yl | $CH_2SO_2CH_3$ | (oil) | |
| 4,5-dichlorothien-2-yl | $CH_2SO_2CH_3$ | (oil) | |
| 4,5-dichlorothien-2-yl | ethynyl | (oil) | 5 |
| 6-chloropyrid-3-yl | ethynyl | (oil) | 5 |

-continued $$A-CH=CH-\underset{\underset{CF_3}{|}}{\overset{\overset{OH}{|}}{C}}-R^8$$

| A | $R^8$ | m.p. (°C.) | Note |
|---|---|---|---|
| 2-chloropyrid-4-yl | ethynyl | (oil) | 5 |

Note 1 Lithium diisopropylamide was used in place of n-butyl-lithium.
Note 5 The butenone was reacted with trimethylsilylacetylene and the trimethylsilyl protecting group was removed by stirring the reaction product with tetra-n-butylammonium fluoride in tetrahydrofuran solution at laboratory temperature.

EXAMPLE 3

A solution of 4-(3,4-dichlorophenyl)-1,2-epoxy-2-trifluoromethylbut-trans-3-ene (1.27 g.) in tetrahydrofuran (20 ml.) was added dropwise to a stirred mixture of pyridine-2-thiol (0.5 g.), sodium hydride (0.22 g. of a 50% dispersion in mineral oil) and tetrahydrofuran (20 ml.), and the mixture was stirred at laboratory temperature for 1 hour and then poured into water. The mixture was extracted with ethyl acetate and the extract was washed with saturated aqueous sodium chloride solution, dried over magnesium sulphate and evaporated to dryness under reduced pressure. The residue was purified by chromatography on a silica gel column using a 3.2 v/v mixture of petroleum ether (b.p. 60°–80° C.) and methylene chloride as eluant. There was thus obtained 4-(3,4-dichlorophenyl)-1-(pyrid-2-yl-thio)-2-trifluoromethylbut-trans-3-en-2-ol, m.p. 64° C.

The epoxybutene used as starting material was obtained as follows:

n-Butyl-lithium (11.6 ml. of a 1.6 molar solution in hexane) was added dropwise to a stirred suspension of trimethylsulphoxonium iodide (4.1 g.) in tetrahydrofuran (200 ml.) which was cooled to −10° C., and the mixture was stirred at that temperature for 2 hours and then added to a stirred solution of 4-(3,4-dichlorophenyl)-1,1,1-trifluorobut-trans-3-en-2-one (Example 1; 2.0 g.) in tetrahydrofuran (100 ml.). The mixture was stirred for 90 minutes, saturated aqueous ammonium chloride solution (75 ml.) was added and the mixture was partitioned between water and ethyl acetate. The layers were separated, the aqueous layer was extracted with ethyl acetate and the combined ethyl acetate solutions were washed with saturated aqueous sodium chloride solution, dried over magnesium sulphate and evaporated to dryness under reduced pressure. The residue was purified by chromatography on a silica gel column using a 4:1 v/v mixture of petroleum ether (b.p. 60°–80° C.) and methylene chloride as eluant. There was thus obtained as an oil 4-(3,4-dichlorophenyl)-1,2-epoxy-2-trifluoromethyl-but-trans-3 ene.

The process described above was repeated using as starting materials the appropriate thiol and the appropriate epoxide, prepared as described above from the appropriate butenone either as described in Example 1 or by the method generally described in Angewandte Chemie (International Edition), 1973, Volume 12, page 845. There were thus obtained the compounds described in the following table:

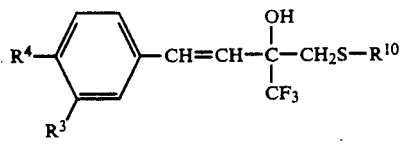

| $R^3$ | $R^4$ | $R^{10}$ | m.p. (°C.) |
|---|---|---|---|
| Cl | Cl | ethyl | (oil) |
| Cl | Cl | n-propyl | (oil) |
| Cl | CN | n-butyl | (oil) |
| Cl | Cl | allyl | (oil) |
| Cl | Cl | 4-fluorophenyl | (oil) |
| H | CN | 4-fluorophenyl | (oil) |
| Cl | CN | 4-fluorophenyl | 110 |
| Cl | Cl | 4-chlorophenyl | (oil) |
| Cl | Cl | 4-nitrophenyl | (oil) |
| Cl | Cl | 3-methylthiophenyl | (oil) |
| Cl | CN | 3-methylthiophenyl | 77 |
| $CF_3$ | CN | 3-methylthiophenyl | 109 |
| Cl | CN | 4-methylthiophenyl | 73 |
| $CF_3$ | CN | 4-methylthiophenyl | (oil) |
| Cl | Cl | 3-methylsulphonylphenyl | (oil) |
| $CF_3$ | CN | 3-methylsulphonylphenyl | 58 |
| $CF_3$ | CN | 4-dimethylaminophenyl | 110–111 |
| Cl | Cl | 4-acetamidophenyl | 55 |
| $CF_3$ | CN | 4-acetamidophenyl | 58–61 |
| Cl | Cl | 4-carboxamidophenyl | (oil) |
| $CF_3$ | CN | 4-carboxamidophenyl | (oil) |
| $CF_3$ | CN | 2-pyridyl | (oil) |
| H | CN | 2-pyridyl | (oil) |
| $CF_3$ | CN | 3-pyridyl | (oil) |
| Cl | Cl | 3-pyridyl | 164 |
| Cl | Cl | 4-pyridyl | 168 |
| $CF_3$ | Cl | 4-pyridyl | 191 |
| $CF_3$ | CN | 4-pyridyl | 193–195 |
| Cl | F | 4-pyridyl | 142 |
| Cl | Cl | 2-quinolyl | 148 |
| Cl | Cl | 4-quinolyl | 126 |
| $CF_3$ | CN | 8-quinolyl | 78 |
| Cl | Cl | 2-methyl-4-quinolyl | 172 |
| Cl | Cl | 7-chloro-4-quinolyl | 191 |
| $CF_3$ | CN | 7-chloro-4-quinolyl | (oil) |
| Cl | Cl | 7-trifluoromethyl-4-quinolyl | 135 |
| Cl | CN | 7-trifluoromethyl-4-quinolyl | 181–184 |
| $CF_3$ | Cl | 7-trifluoromethyl-4-quinolyl | 156 |
| $CF_3$ | CN | 7-trifluoromethyl-4-quinolyl | 156 |
| Cl | Cl | 2-imidazolyl | 141 |
| $CF_3$ | CN | 2-imidazolyl | (oil) |
| $CF_3$ | F | 2-imidazolyl | (oil) |
| $CF_3$ | F | 1-methyl-2-imidazolyl | (oil) |
| Cl | Cl | 1-methyl-2-imidazolyl | 100 |
| $CF_3$ | CN | 1-methyl-2-imidazolyl | 108 |
| Cl | Cl | 2-thiazolyl | (oil) |
| $CF_3$ | F | 2-thiazolyl | (oil) |
| $CF_3$ | CN | 2-thiazolyl | (oil) |
| Cl | F | 2-thiazolyl | (oil) |
| Cl | Cl | 1,2,4-triazol-3-yl | 72 |
| Cl | Cl | 2-pyrimidinyl | 94 |
| Cl | F | 2-pyrimidinyl | (oil) |
| $CF_3$ | F | 2-pyrimidinyl | (oil) |
| $CF_3$ | CN | 2-pyrimidinyl | (oil) |
| Cl | Cl | 4-methyl-2-pyrimidinyl | 89 |
| $CF_3$ | CN | 4-methyl-2-pyrimidinyl | (oil) |
| Cl | Cl | 4-hydroxy-2-pyrimidinyl | 96 |
| $CF_3$ | CN | 4-hydroxy-2-pyrimidinyl | (oil) |
| Cl | Cl | 4-amino-2-pyrimidinyl | 119 |
| $CF_3$ | CN | 4-amino-2-pyrimidinyl | (oil) |
| $CF_3$ | CN | 4,6-dimethyl-2-pyrimidinyl | (oil) |
| Cl | Cl | purin-6-yl | 146 |
| $CF_3$ | CN | purin-6-yl | 110 |
| $CF_3$ | CN | 1H-pyrazolo[3,4-d]-pyrimidin-4-yl | 208 |
| Cl | Cl | 2-chloro-6-methoxy acridin-9-yl | 211 |
| Cl | Cl | 2-amino-6-purinyl | 162 |
| Cl | Cl | 4,6-dimercapto-1,3,5-triazin-2-yl | 240 (decomp.) |
| Cl | Cl | benzimidazolo[1,2-c]-quinazolin-6-yl | 198 |
| $CF_3$ | CN | 4-amino-2-pyrimidinyl | (oil) |

EXAMPLE 4

Magnesium chloride (0.4 g.) was added to a solution of 4-(3,4-dichlorophenyl)-1,2-epoxy-2-trifluoro methyl-but-trans-3-ene (Example 3; 0.25 g.)in diethyl ether (10 ml.) and the suspension was stirred at laboratory temperature for 4 days. Methanol (0.5 ml.) was added and the mixture was stirred for 2 days and then poured into water. The mixture was extracted with methylene chloride and the extract was washed with water and then with saturated aqueous sodium chloride solution, dried over magnesium sulphate and evaporated to dryness under reduced pressure. The residue was purified by chromatography on a silica gel column using a 4:1 v/v mixture of petroleum ether (b.p. 60°–80° C.) and methylene chloride as eluant. There was thus obtained 1-chloro-4- (3,4-dichlorophenyl)-2-trifluoromethylbut-trans-3-en-2-ol, m.p. 64° C.

EXAMPLE 5

A mixture of 1-(3,4-dichlorophenyl)-4,4,4-trifluoro-3-trifluoromethylbutane-1,3-diol (10.0 g.) and p-toluenesulphonic acid (2.0 g.) was heated at 140° C. for 15 minutes; cooled to laboratory temperature and partitioned between water and ethyl acetate. The ethyl acetate layer was washed with saturated aqueous sodium bicarbonate solution and then with saturated aqueous sodium chloride solution, dried over magnesium sulphate and evaporated to dryness under reduced pressure. The residue was purified by chromatography on a silica gel column using a 9:1 v/v mixture of petroleum ether (b.p. 60°-80° C.) and methylene chloride as eluant, and there was thus obtained as an oil 4-(3,4-dichlorophenyl)1,1,1-trifluoro-2-trifluoromethylbut-trans-3-en-2-ol.

The butane-1,3-diol used as starting material was obtained as follows:

A solution of 3,4-dichloroacetophenone (5.0 g.)in tetrahydrofuran (50 ml.) was added dropwise to a stirred solution of lithium diisopropylamide (prepared from n-butyl-lithium [19.8 ml. of a 1.6 molar solution in hexane] and diisopropylamine (4.3 ml.) in tetrahydrofuran (200 ml.) during 10 minutes at 0° C.) which was cooled to −78° C., and the mixture was stirred at −78° C. for 30 minutes and then at −50° C. for 45 minutes, and then recooled to −78° C. Anhydrous hexafluoroacetone (10 ml., generated by treating the sesquihydrate with concentrated sulphuric acid) was distilled into the mixture, which was then stirred for 1 hour at −78° C. Methanol (10 ml.) and saturated aqueous ammonium chloride solution (50 ml.) were added, the mixture was allowed to warm up to laboratory temperature and was poured into water (250 ml.) and the mixture was extracted with diethyl ether. The extract was washed with saturated aqueous sodium chloride solution, dried over magnesium sulphate and evaporated to dryness under reduced pressure, and there was thus obtained as an oil 1-(3,4-dichlorophenyl)-4,4,4-trifluoro-3-hydroxy-3-trifluoromethylbutan-1-one which was used without further purification.

Sodium borohydride (3.2 g.) was added in portions during 15 minutes to a stirred solution of the total amount obtained of the above compound in ethanol (200 ml.) which was cooled to 0° C., and the mixture was stirred at 0° C. for 1 hour. Concentrated aqueous hydrochloric acid was added to neutralise the mixture, the ethanol was removed by evaporation under reduced pressure and the residue was partitioned between diethyl ether and water. The ethereal layer was washed with saturated aqueous sodium chloride solution, dried over magnesium sulphate and evaporated to dryness under reduced pressure, and there was thus obtained as residue 1-(3,4-dichlorophenyl)-4,4,4-trifluoro-3-trifluoromethylbutane-1,3-diol which was used without further purification.

The process described above was repeated using the appropriate acetophenone as initial starting material and there were thus obtained the compounds described in the following table:

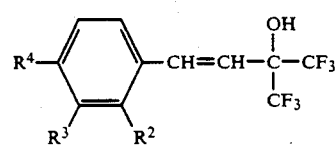

| $R^2$ | $R^3$ | $R^4$ | m.p. (°C.) |
|---|---|---|---|
| H | H | Cl | (oil) |
| H | H | CN | 115–117 |
| H | Cl | H | (oil) |

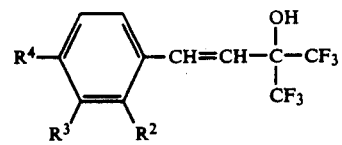

| $R^2$ | $R^3$ | $R^4$ | m.p. (°C.) |
|---|---|---|---|
| Cl | H | Cl | (oil) |

The process described above was repeated using 3,4-dichloropropiophenone in place of 3,4-dichloroacetophenone as initial starting material. There was thus obtained as an oil 4-(3,4-dichlorophenyl)-1,1,1-trifluoro-3-methyl-2-trifluoromethylbut-trans-3-en-2-ol.

EXAMPLE 6

A solution of 1-(3,4-dichlorophenyl)-3-trifluoromethylpent-trans-1-en-4-yn-3-ol (Example 2; 0.8 g.) in methanol (5 ml.) was added to a stirred solution of mercuric oxide (0.6 g.) in 4% w,/v aqueous sulphuric acid (50 ml.) which was heated to 60° C., and the mixture was stirred at 60° C. for 30 minutes, cooled to laboratory temperature and extracted with ethyl acetate. The extract was washed with saturated aqueous sodium chloride solution, dried over magnesium sulphate and evaporated to dryness under reduced pressure, and the residue was purified by chromatography on a silica gel column using a 3:2 v/v mixture of methylene chloride and petroleum ether (b.p. 60°-80° C.) as eluant. There was thus obtained as an oil 5-(3,4-dichlorophenyl)-3-hydroxy-3-trifluoromethylpent-trans-4-en-2-one.

The process described above was repeated using the appropriate pentenynol described in Example 2 or Example 8 as starting material, and there were thus obtained the compounds described in the following table:

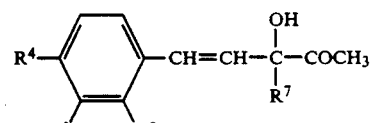

| $R^2$ | $R^3$ | $R^4$ | $R^7$ | m.p. (°C.) |
|---|---|---|---|---|
| H | H | CN | $CF_3$ | (oil) |
| H | CN | H | $CF_3$ | 88–89 |
| H | Cl | F | $CF_3$ | (oil) |
| F | H | F | $CF_3$ | (oil) |
| H | Cl | CN | $CF_3$ | 104–105 |
| H | $CF_3$ | H | $CF_3$ | 61–63 |
| H | F | CN | $CF_3$ | 75.5–76.5 |
| H | CN | Cl | $CF_3$ | (oil) |
| H | $CF_3$ | F | $CF_3$ | (oil) |
| H | $CF_3$ | Cl | $CF_3$ | (oil) |
| H | $CF_3$ | $CO_2$ | $CF_3$ | 96 |
| H | $CF_3$ | CN | $CH_3$ | (oil) |
| H | Cl | Cl | $CH_2Cl$ | (oil) |
| (4,5-dichlorothien-2-yl) | | | $CF_3$ | (oil)* |
| (6-chloropyrid-3-yl) | | | $CF_3$ | (oil)* |

*The 2-$R^2$-3-$R^3$-4-$R^4$-phenyl group is replaced by the named heterocyclyl group.

EXAMPLE 7

A solution of potassium peroxymonosulphate (1.9 g.) in water (14 ml.) was added to a stirred solution of 4-(3,4-dichlorophenyl)-1-(pyrid-2-ylthio)-2-trifluoromethylbut-trans-3-en-2-ol (Example 3; 0.4 g.) in methanol (14 ml.) and the mixture was stirred at laboratory temperature for 16 hours, diluted with water (20 ml.) and extracted with ethyl acetate. The extract was washed with saturated aqueous sodium chloride solution, dried over magnesium sulphate and evaporated to dryness under reduced pressure, and the residue was purified by chromatography on a silica gel column using a 7.3 v/v mixture of petrolium ether (b.p. 60°-80° C.) and ethyl acetate as eluant. There was thus obtained as a gum 4-(3,4-dichlorophenyl)-1-(pyrid-2-ylsulphonyl)-2-trifluoromethylbut-trans-3-en-2-ol.

The process described above was repeated using the appropriate thio-compound described in Example 3 as starting material, and there were thus obtained the compounds described in the following table:

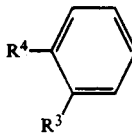

| $R^3$ | $R^4$ | $R^{10}$ | m.p. (°C.) |
|---|---|---|---|
| Cl | Cl | ethyl | 88 |
| Cl | Cl | n-propyl | 102 |
| Cl | Cl | allyl | 87 |
| Cl | Cl | 4-fluorophenyl | 165 |
| H | CN | 4-fluorophenyl | (oil) |
| Cl | Cl | 4-chlorophenyl | 133 |
| Cl | Cl | 4-nitrophenyl | 201 |
| H | CN | 2-pyridyl | (oil) |
| Cl | Cl | 2-thiazolyl | 81 |
| Cl | F | 2-thiazolyl | (oil) |
| Cl | Cl | 3-methylsulphonyl-phenyl | 88 |
| Cl | CN | 3-methylsulphonyl-phenyl | 95 |
| Cl | CN | 4-methylsulphonyl-phenyl | 172 |
| Cl | Cl | 7-trifluoromethyl-quinol-4-yl | 187 |
| Cl | Cl | 2-chloro-6-methoxy-acridin-9-yl | 262 |
| Cl | Cl | pyrid-4-yl* | 161 |
| Cl | F | pyrid-4-yl* | 148 |

*Under the conditions described above the oxidation stopped at the sulphoxide stage and these two compounds have the group —CH$_2$SOR$^{10}$ in place of —CH$_2$SO$_2$R$^{10}$

EXAMPLE 8

A solution of s-butyllithium (8.6 ml. of a 1.3 molar solution in cyclohexane) was added dropwise to a stirred suspension of methyltriphenylphosphonium bromide (2.0 g.) in tetrahydrofuran (20 ml.) which was cooled to −78° C. under an atmosphere of argon, and the mixture was stirred at −78° C. for 1 hour, at laboratory temperature for 3 hours and was then recooled to −78° C. Trifluoroacetone (0.5 ml.) was added dropwise, the mixture was stirred for 15 minutes, n-butyllithium (3.8 ml. of a 1.6 molar solution in hexane) was added dropwise and the mixture was stirred for a further 15 minutes still at −78° C. A solution of 3-chloro-4-cyanobenzaldehyde (0.95 g.) in tetrahydrofuran (12 ml.) was added dropwise and the mixture was stirred for 10 minutes at −78° C., 2 hours at 0° C. and 12 hours at laboratory temperature. Saturated aqueous sodium chloride solution (20 ml.) was added, the layers were separated and the aqueous layer was extracted twice with diethyl ether (25 ml. each time). the combined organic solutions were dried and evaporated to dryness and the residual oil was purified by flash chromatography on a silica gel column using a 3.1 v/v mixture of petroleum ether (b.p. 60°-80° C.) and ethyl acetate as eluant. The product obtained was crystallised from a 1:1 v/v mixture of toluene and petrolium ether (b.p. 60°-80° C.) and there was thus obtained 4-(3-chloro-4-cyanophenyl)-2-trifluoromethylbut-trans-3-en-2-ol, m.p. 88°-92° 1 C.

The process described above was repeated using the appropriate aldehyde in place of 3-chloro-4- cyanobenzaldehyde, and the appropriate ketone of the formula R$^7$COR$^8$ in place of trifluoroacetone, as starting materials, and there were thus obtained the compounds described in the following table:

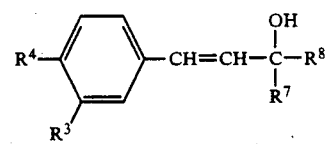

| $R^3$ | $R^4$ | $R^7$ | $R^8$ | m.p. (°C.) | Note |
|---|---|---|---|---|---|
| Cl | NO$_2$ | CF$_3$ | CH$_3$ | (oil) | |
| CF$_3$ | NO$_2$ | CF$_3$ | CH$_3$ | 67-69 | |
| CF$_3$ | Cl | CF$_3$ | CH$_3$ | (oil) | |
| CF$_3$ | CN | CF$_3$ | CH$_3$ | 112-115 | |
| CH$_3$S | CN | CF$_3$ | CH$_3$ | 113-115 | |
| CH$_3$SO | CN | CF$_3$ | CH$_3$ | 115-120 | 1 |
| CH$_3$SO$_2$ | CN | CF$_3$ | CH$_3$ | 107-108 | 2 |
| CH$_3$O | CN | CF$_3$ | CH$_3$ | 104-106 | |
| (5-cyanothien-2-yl) | | CF$_3$ | CH$_3$ | (oil) | 3 |
| (5-nitrothien-2-yl) | | CF$_3$ | CH$_3$ | (oil) | 3 |
| (2-chloropyrid-4-yl) | | CF$_3$ | CH$_3$ | (oil) | 3 |
| (6-chloropyrid-3-yl) | | CF$_3$ | CH$_3$ | (oil) | 3 |
| Cl | Cl | CF$_3$ | C$_2$H$_5$ | (oil) | |
| CF$_3$ | Cl | CF$_3$ | C$_2$H$_5$ | (oil) | |
| CN | H | CF$_3$ | C$_2$H$_5$ | 83-85 | |
| H | CN | CF$_3$ | C$_2$H$_5$ | (oil) | |
| CH$_3$ | CN | CF$_3$ | C$_2$H$_5$ | 87-88 | |
| F | CN | CF$_3$ | C$_2$H$_5$ | (oil) | |
| Cl | CN | CF$_3$ | C$_2$H$_5$ | 106 | |
| Br | CN | CF$_3$ | C$_2$H$_5$ | (oil) | |
| CF$_3$ | CN | CF$_3$ | C$_2$H$_5$ | 120-121 | |
| CF$_3$ | CN | CF$_3$ | n-propyl | 139-140 | |
| CF$_3$ | CN | CF$_3$ | isopropyl | 99-101 | |
| CF$_3$ | CN | CF$_3$ | n-butyl | 100-102 | |
| CF$_3$ | CN | CF$_3$ | n-hexyl | 84 | |
| CF$_3$ | CN | CF$_3$ | cyclopropyl | 119-120 | |
| CF$_3$ | CN | CF$_3$ | CH$_2$CH$_2$C$_6$H$_5$ | 116-118 | |
| CF$_3$ | CN | CF$_3$ | ethynyl | 121-123 | 4 |
| Cl | CN | CF$_3$ | ethynyl | 116-117 | 4 |
| CH$_3$O | CN | CF$_3$ | ethynyl | 100-101 | 4 |
| Cl | NO$_2$ | CF$_3$ | ethynyl | (oil) | 4 |
| F | CN | CF$_3$ | ethynyl | 92-94 | 4 |
| CF$_3$ | CN | C$_2$F$_5$ | CH$_3$ | 106-107 | |
| CF$_3$ | CN | methyl | C$_2$H$_5$ | (oil) | |
| Cl | F | CF$_3$ | isopropyl | (oil) | |

Note 1
Prepared by oxidation of the corresponding compound wherein R$^3$ is CH$_3$S(immediately preceding compound in table) with sodium metaperiodate by a similar process to that described in Example 5 of European Specification No. 100172.

Note 2
Prepared by oxidation of the corresponding compound wherein R$^3$ is CH$_3$S with m-chloroperbenzoic acid by a similar process to that described in Example 6 of European Specification No. 100172.

Note 3
The 3-R$^3$-4-R$^4$-phenyl group is replaced by the named heterocyclic group.

Note 4
The ketone starting material used was trifluoromethyl 2-trimethylsilylethynyl ketone (b.p. 110-115° C.), the trimethylsilyl group being removed as described in Note 5 to Example 2.

The ketones used as starting materials were prepared by the general process described in the Journal of the Chemical Society, 1956, page 835. Cyclopentyl trifluoromethyl ketone has b.p. 118°-120° C.

EXAMPLE 9

The process described in Example 3 was repeated except that the pyridine-2-thiol and sodium hydride were replaced by either dimethyl sulphone and n-butyl-lithium (as in Example 1), or by acetonitrile and lithium diisopropylamide. There were thus obtained respectively 5-(3,4-dichlorophenyl)-1-methylsulphonyl-3-trifluoromethylpent-trans-4-en-3-ol, m.p 71° C. and 5-(3,4-dichlorophenyl-1-cyano-3-trifluoromethylpent-trans-4-en-3-ol, m.p 68° C.

EXAMPLE 10

The process described in Example 3 was repeated except that acetamide was used as starting material in place of pyridine-2-thiol. The product was purified by chromatography on a silica gel column using a 3:2 v/v mixture of petroleum ether (b.p. 60°-80° C.) and ethyl acetate as eluant, and there was thus obtained N-[4-(3,4-dichlorophenyl)-2-hydroxy-2-trifluoromethyl-but-trans-3-enyl]acetamide, m.p. 94° C.

EXAMPLE 11

The process described in Example 3 was repeated except that concentrated aqueous ammonia solution was used in place of the mixture of pyridine-2-thiol and sodium hydride. There was thus obtained 1-amino-4-(3,4-dichlorophenyl)-2-trifluoromethylbut-trans-3-en-2-ol, m.p 96° C.

EXAMPLE 12

Pyridine (0.053 g.) and methanesulphonyl chloride (0.05 ml.) were successively added to a stirred solution of 1-amino-4-(3,4-dichlorophenyl)-2-trifluoromethyl-but-trans-3-en-2-ol (Example 11; 0.2 g.) in methylene chloride (2 ml.) and the mixture was stirred at laboratory temperature for 30 minutes and then evaporated to dryness. The residue was purified by chromatography on a silica gel column using a 3:2 v/v mixture of petroleum ether (b.p. 60°-80° C.) and ethyl acetate as eluant, and there was thus obtained N-[4-(3,4-dichlorophenyl)-2-hydroxy-2-trifluoromethylbut-trans-3-enyl]methanesulphonamide, m.p. 151° C.

The process described above was repeated using methyl chloroformate in place of methanesulphonyl chloride. There was thus obtained methyl N-[4-(3,4-dichlorophenyl)-2-hydroxy-2-trifluoromethylbut-3-enyl]carbamate, m.p. 132° C.

EXAMPLE 13

A mixture of 4-(3,4-dichlorophenyl)-1-methylsulphinyl-1-methylthio-2-trifluoromethylbut-trans-3-en-2-ol (Example 2; 0.3 g.), triethyl orthoformate (1.12 g.), ethanol (5 ml.) and concentrated sulphuric acid (0.01 ml.) was heated under reflux for 4 hours, cooled to laboratory temperature and poured into water (20 ml.) The mixture was extracted with ethyl acetate (20 ml.) and the extract was washed with saturated aqueous sodium chloride solution, dried over magnesium sulphate and evaporated to dryness under reduced pressure. The residue was dissolved in tetrahydrofuran (5 ml.), 60% aqueous sulphuric acid (1 ml.) was added and the solution was freed from air and then heated under reflux under an atmosphere of argon for 1 hour. Water (15 ml.) was added, the mixture was extracted with ethyl acetate, and the extract was washed with water and then with saturated aqueous sodium chloride solution, dried over magnesium sulphate and evaporated to dryness under reduced pressure. The residue was purified by chromatography on a silica gel column using a 3:2 v/v mixture of methylene chloride and petroleum ether (b.p. 60°-80° C.) as eluant. There was thus obtained as an oil 4-(3,4-dichlorophenyl)-2-hydroxy-2-trifluoromethylbut-trans-3-en-1-one.

The process described above was repeated using 6-(3,4-dichlorophenyl)-3-methylsulphinyl-3-methylthio-4-trifluoro-methylhex-trans-5-en-4-ol (Example 2) as starting material, and there was thus obtained as an oil 6-(3,4-dichlorophenyl)-4-hydroxy-4-trifluoromethylhextrans-5-en-3-one.

EXAMPLE 14

A solution of 4-(3,4-dichlorophenyl)-2-hydroxy-2-trifluoromethylbut-trans-3-en-1-one (Example 13; 0.8 g.) in ethanol (5 ml.) was added dropwise to a stirred solution of sodium borohydride (0.3 g.) in ethanol (5 ml.), and the mixture was stirred at laboratory temperature for 2 hours, acidified with aqueous 2N-hydrochloric acid (1 ml.) and poured into water (20 ml.). The mixture was extracted with ethyl acetate and the extract was washed with saturated aqueous sodium chloride solution, dried over magnesium sulphate and evaporated to dryness under reduced pressure. The residue was purified by chromatography on a silica gel column using a 40:1 v/v mixture of methylene chloride and ethyl acetate as eluant. There was thus obtained 4-(3,4-dichlorophenyl)-2- trifluoromethylbut-trans-3-ene-1,2-diol, m.p. 162° C.

The process described above was repeated using either 5-(3,4-dichlorophenyl)-3-hydroxy-3-trifluoromethylpent-trans-4-en-2-one (Example 6) or 6-(3,4-dichlorophenyl)-4-hydroxy-4-trifluoromethylhex-trans-5-en-3-one (Example 13) as starting materials, and there were respectively obtained 5-(3,4-dichlorophenyl)-3-trifluoromethylpent-trans-4-ene-2,3-diol, m.p. 65° C. and 6-(3,4-dichlorophenyl)-4-trifluoromethylhex-trans-5-ene-3,4-diol, as an oil.

EXAMPLE 15

A complex of potassium cyanide and 18-crown-6-(0.002 g.) was added to a stirred solution of 1,1,1-trifluoro-4-(3,4-dichlorophenyl)but-trans-3-en-2-one (Example 1; 1 g.) in trimethylsilyl cyanide (0.79 g.) and the mixture was stirred at laboratory temperature for 1 hour and then evaporated to dryness under reduced pressure. A solution of the residue in tetrahydrofuran (2 ml.) was added to a saturated solution of hydrogen chloride in methanol (50 ml.) and the mixture was stirred at laboratory temperature for 17 hours and then poured into ice-water. The mixture was extracted with ethyl acetate and the extract was washed with water and then with saturated aqueous sodium chloride solution, dried over magnesium sulphate and evaporated to dryness under reduced pressure. The residue was purified by chromatography on a silica gel column using a 20.3 v/v mixture of methylene chloride and ethyl acetate as eluant. There was thus obtained 4-(3,4-dichlorophenyl)-2-hydroxy-2-trifluoromethylbut-trans-3-enamide, m.p.149° C.

EXAMPLE 16

Acetic anhydride (0.2 g.) and pyridine (0.15 g.) were successively added to a stirred solution of 4-(3,4-dichlorophenyl)-2-hydroxy-2-trifluoromethylbut-trans-3-enoic acid (0.2 g.) in ethyl acetate (5 ml.) and the mixture was stirred at laboratory temperature for 17 hours and then evaporated to dryness under reduced pressure. The residue was dissolved in methylene chloride (5 ml.), pyridine (0.1 g.) and thionyl chloride (0.15 g.) were added and the mixture was stirred at laboratory temperature for 1 hour. Monomethylamine gas was then passed through the mixture until it was saturated, and the mixture was stirred at laboratory temperature for 1 hour and then poured into water. The mixture was extracted with methylene chloride and the extract was washed with saturated aqueous sodium chloride solution, dried over magnesium sulphate and evaporated to dryness under reduced pressure. Aqueous 2N-sodium hydroxide solution (0.2 ml.) was added to a stirred solution of the residue in ethanol (5 ml.) and the mixture was stirred at laboratory temperature for 90 minutes, diluted with water and extracted with ethyl acetate. The extract was washed with saturated aqueous sodium chloride solution, dried over magnesium sulphate and evaporated to dryness under reduced pressure. The residue was purified by chromatography on a silica gel column using a 20:1 v/v mixture of methylene chloride and ethyl acetate as eluant. There was thus obtained 4-(3,4-dichlorophenyl)-2-hydroxy-N-methyl-2-trifluoromethylbut-trans-3-enamide, m.p. 165° C.

The process described above was repeated using dimethylamine in place of monomethylamine, and there was thus obtained 4-(3,4-dichlorophenyl)-2-hydroxy-N,N-dimethyl- 2-trifluoromethylbut-trans-3-enamide, m.p.168° C.

The 4-(3,4-dichlorophenyl)-2-hydroxy-2-trifluoromethylbut-trans-3-enoic acid used as starting material was obtained as follows:

Concentrated sulphuric acid (1 ml.) was added to a solution of 4-(3,4-dichlorophenyl)-2-hydroxy-2-trifluoromethylbut-trans-3-enamide (Example 15; 0.3 g.) in ethanol (20 ml.) and the mixture was heated under reflux for 24 hours, diluted with water and extracted with ethyl acetate. The extract was washed with saturated aqueous sodium chloride solution, dried over magnesium sulphate and evaporated to dryness under reduced pressure. Aqueous 2N-sodium hydroxide solution (0.7 ml.) was added to a stirred solution of the residue in ethanol (10 ml.) and the mixture was stirred at laboratory temperature for 17 hours and then poured into water. The mixture was washed with ethyl acetate and the aqueous layer was then acidified with aqueous 2N-hydrochloric acid and extracted with ethyl acetate. The extract was washed with saturated aqueous sodium chloride solution, dried over magnesium sulphate and evaporated to dryness under reduced pressure. There was thus obtained as residual solid 4-(3,4-dichlorophenyl)-2-hydroxy-2-trifluoromethylbut-trans-3-enoic acid which was used without further purification.

EXAMPLE 17 t-Butyl-lithium (1.1 ml. of a 1.8 molar solution in diethyl ether) was added dropwise to a solution of trans-1-bromo-2-(3,4-dichlorophenyl)cyclopropane (0.53 g.) in a mixture of diethyl ether (18 ml.) and tetrahydrofuran (2 ml.) which was maintained at −100° C., and the mixture was stirred at that temperature for 1 hour. A solution of 1,1,1-trifluoro-4-trimethylsilylbut-3-yn-2-one (0.39 g.) in tetrahydrofuran (5 ml.) was added dropwise, the mixture was stirred at −100° C. for 2 hours and a mixture of methanol (1 ml.) and aqueous 2N-hydrochloric acid (1 ml.) was added. The mixture was allowed to warm up to laboratory temperature and was poured into water, and the mixture was extracted with ethyl acetate. The extract was washed with saturated aqueous sodium chloride solution, dried over magnesium sulphate and evaporated to dryness under reduced pressure. Tetra-n-butylammonium fluoride (0.16 g.) was added to a stirred solution of the residue in tetrahydrofuran (25 ml.) and the mixture was stirred at laboratory temperature for 4 hours, diluted with water (100 ml.) and extracted with ethyl acetate. The extract was washed with saturated aqueous sodium chloride solution, dried over magnesium sulphate and evaporated to dryness under reduced pressure. The residue was purified by chromatography on a silica gel column using an 11:9 v/v mixture of petroleum ether (b.p. 60°-80° C.) and methylene chloride as eluant. There was thus obtained as an oil 2-[2-(3,4-dichlorophenyl)cyclopropyl]-1,1,1-trifluorobut-3-yn-2-ol.

The cyclopropane used as starting material was obtained as follows:

Potassium t-butoxide (5.1 g.) was added to a stirred mixture of 3,4-dichlorophenylethylene (6.1 g.), bromoform (8.9 g.) and petroleum ether (b.p. 60°-80° C.; 100 ml.) which was cooled to −30° C., and the mixture was stirred at that temperature for 30 minutes, then at laboratory temperature for 17 hours and then poured into water. The mixture was extracted with ethyl acetate and the extract was washed with saturated aqueous sodium chloride solution, dried over magnesium sulphate and evaporated to dryness under reduced pressure The residue was purified by chromatography on a silica gel column using petroleum ether (b.p. 40°-60° C.) as eluant, and there was thus obtained as an oil 1,1-dibromo-2-(3,4-dichlorophenyl)cyclopropane.

n-Butyl-lithium (14.7 ml. of a 1.6 molar solution in hexane) was added dropwise to a stirred solution of the above cyclopropane (8.1 g.) in tetrahydrofuran (100 ml.) which was maintained at −100° C., and the mixture was stirred at that temperature for 30 minutes. A mixture of methanol (2.5 ml.) and aqueous 2N-hydrochloric acid (2.5 ml.) was added and the mixture was allowed to warm up to laboratory temperature and was then poured into water. The mixture was extracted with ethyl acetate and the extract was washed with saturated aqueous sodium chloride solution, dried over magnesium sulphate and evaporated to dryness under reduced pressure. The residue was purified by chromatography on a silica gel column using petroleum ether (b.p. 40°-60° C.) as eluant. There was thus obtained as an oil trans-1-bromo-2-(3,4-dichlorophenyl)cyclopropane, which was used without further purification.

EXAMPLE 18

A mixture of 4-iodo-2-trifluoromethylbenzonitrile (1.65 g.), bis-(triphenylphosphine)palladium (II) chloride (0.07 g.), cuprous iodide (0.01 g.), 1-methylsulphonyl-2-trifluoromethylbut-3-yn-2-ol (1.2 g.) and diethylamine (25 ml.) was stirred at laboratory temperature under an atmosphere of argon for 4 hours and then evaporated to dryness. The residue was purified by flash chromatography on a silica gel (Merck 9385) column using a 1:1 v/v mixture of ethyl acetate and petroleum ether (b.p. 60°-80° C.) as eluant, and the product was crystallised from a 4:1 v/v mixture of petroleum ether (b.p. 60°-80° C.) and ethyl acetate. There was thus obtained 4-(4-cyano-3-trifluoromethylphenyl)-1-methyl-sulphonyl-2-trifluoromethylbut-3-yn-2-ol, m.p. 134°-136° C.

The 1-methylsulphonyl-2-trifluoromethylbut-3-yn-2-ol used as starting material was obtained as follows:

n-Butyl-lithium (10.6 ml. of a 1.6 molar solution in hexane) was added dropwise to a solution of dimethyl sulphone (1.6 g.) in tetrahydrofuran (50 ml.) which was maintained at −20° C. under an atmosphere of argon, and the mixture was stirred at that temperature for 1 hour and then cooled to −78° C. A solution of 1,1,1-trifluoro-4-trimethylsilylbut-3-yn-2-one (3.0 g.) in tetrahydrofuran (10 ml.) was added dropwise and the mixture was stirred at −78° C. for 90 minutes. Water (0.5 ml.) was added and the mixture was allowed to warm up to laboratory temperature and was then evaporated to dryness under reduced pressure. The residue was purified by flash chromatography on a silica gel (Merck 9385) column using a 1:1 v/v mixture of ethyl acetate and petroleum ether (b.p. 60°–80° C.) as eluant. There was thus obtained 1-methylsulphonyl-2-trifluoromethyl-4-trimethylsilylbut-3-yn-2-ol, m.p. 61°–64° C.

A solution of potassium hydroxide (0.5 g.) in water (0.5 ml.) was added to a stirred solution of the above compound (1.5 g.) in methanol (10 ml.) and the mixture was stirred at laboratory temperature for 10 minutes and evaporated to dryness. The residue was subject to flash chromatography on a silica gel (Merck 9385) column using a 1:1 v/v mixture of ethyl acetate and petroleum ether (b.p. 60°–80° C.) as eluant. The product was crystallised from toluene and there was thus obtained 1-methylsulphonyl-2-trifluoromethylbut-3-yn-2-ol, m.p. 89°–91° C.

EXAMPLE 19

A solution of 4-(4-cyano-3-trifluoromethylsulphonyl-2-trifluoromethylbut-3-yn-2-ol (Example 18; 0.5 g.) and potassium hydroxide (0.015 g.) in methanol (20 ml.) was shaken with a 5% palladium-on-charcoal catalyst (0.025 g.) in an atmosphere of hydrogen at laboratory temperature until uptake of hydrogen ceased. The mixture was filtered, the filtrate was evaporated to dryness and the residue was crystallised from toluene. There was thus obtained 4-(4-cyano-3-trifluoromethylphenyl)-1-methylsulphonyl-2-trifluoromethylbut-cis-3en-2-ol, m.p. 124°–125° C.

What we claim is:

1. A compound of the formula

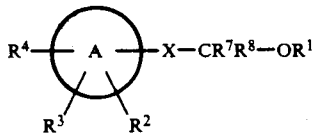

wherein X has the formula $$-CR^5=CR^6-$$

$$-C\equiv C-$$

or

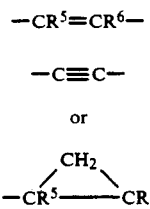

wherein ring A is phenyl, naphthyl, pyridyl, quinolyl or thienyl; wherein $R^1$ is hydrogen, alkanoyl of up to 6 carbon atoms or aroyl of up to 10 carbon atoms; wherein $R^2$, $R^3$ and $R^4$, which may be the same of different, each is an electron withdrawing substituent selected from halogeno, nitro, cyano and trifluoromethyl, and alkylthio, alkylsulphinyl and alkylsulphonyl each of up to 6 carbon atoms, or each is hydrogen or alkyl, alkoxy or dialkylamino each of up to 6 carbon atoms, provided that when ring A is phenyl or naphthyl at least one of $R^2$, $R^3$ and $R^4$ is an electron-withdrawing substituent; wherein $R^5$ and $R^6$, which may be the same or different, each is hydrogen, halogeno or alkyl of up to 6 carbon atoms; wherein $R^7$ is halogenoalkyl of up to 6 carbon atoms; and wherein $R^8$ is carbamoyl, alkyl, cycloalkyl, alkenyl, alkynyl, halogenoalkyl, halogenoalkenyl, halogenoalkynyl or alkanoyl each of up to 6 carbon atoms, or alkylcarbamoyl or dialkylcarbamoyl wherein each alkyl is of up to 6 carbon atoms, or aroyl of up to 10 carbon atoms; or wherein $R^8$ is alkyl or alkenyl each of up to 6 carbon atoms which bears one or more substituents selected from cyano, carbamoyl, amino and hydroxy, alkanoyl, alkoxy, alkylthio, alkenylthio, alkylsulphinyl, alkenylsulphinyl, alkylsulphonyl, alkenylsulphonyl, alkanoylamino, alkoxycarbonylamino and alkylsulphonamido each of up to 6 carbon atoms, alkylamino, dialkylamino and dialkylsulphamoyl wherein each alkyl is of up to 6 carbon atoms, aroyl, aryl, arylthio, arylsulphinyl and arylsulphonyl each of up to 10 carbon atoms and heterocyclylthio, heterocyclylsulphinyl and heterocyclylsulphonyl and wherein the heterocyclyl group in $R^8$ is a 5- or 6-membered saturated or unsaturated heterocyclic which contains one, two or three hetero atoms selected from oxygen, nitrogen and sulphur, which heterocyclic is a single ring or is fused to one or two benzo-rings or to another heterocyclic ring as defined above, and which heterocyclic is unsubstituted or bears substituents $R^2$, $R^3$ and $R^4$ as defined above, or may also bear one or more hydroxy, mercapto or amino substituents; or wherein $R^8$ has the formula

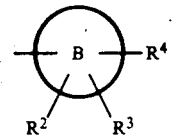

wherein ring B is phenyl or naphthyl or ring B is pyridyl or thiazolyl which is unsubstituted or bears a halogeno or trifluoromethyl substituent, or is unsubstituted 1,3-dithian-2-yl.

2. A compound of the formula stated in claim 1 wherein X is $-CR^5=CR^6-$, wherein ring A is phenyl, wherein one or two (the same or different) of $R^2$, $R^3$ and $R^4$ are fluoro, chloro, cyano, trifluoromethyl or nitro, the others of $R^2$, $R^3$ and $R^4$ being hydrogen, wherein $R^1$, $R^5$ and $R^6$ are all hydrogen, wherein $R^7$ is trifluoromethyl, pentafluoroethyl, heptafluoropropyl, chloromethyl or dichloromethyl, wherein $R^8$ is methyl, ethyl, n-propyl, isopropyl, n-butyl, cyclopropyl, cyclopentyl, trifluoromethyl, chloromethyl, dichloromethyl, ethynyl, chloroethynyl, acetyl or propionyl or is methylene (13 $CH_2-$) substituted by cyano, hydroxy, carbamoyl, formyl, acetyl, alkylthio, alkenylthio, alkylsulphonyl or alkenylsulphonyl each of up to 6 carbon atoms, phenylthio or phenylsulphonyl which itself is unsubstituted or bears a fluoro, chloro, nitro, carbamoyl, acetamido, methylthio or methylsulphonyl substituent, pyridyl, quinolyl, pyrimidinyl, purinyl, pyrazolopyrimidinyl, thiazolyl, imidazolyl or triazolyl any of which is unsubstituted or bears a hydroxy, mercapto, amino, chloro, trifluoromethyl or methyl substituent, and wherein the —CR$^5$=CR$^6$— group is in the trans- configuration.

3. A pharmaceutical or veterinary composition having antiandrogenic properties which comprises a compound claimed in claim 1 in association with a pharmaceutically-acceptable diluent or carrier.

4. A composition as claimed in claim 3 which is in a form suitable for oral dosage, as a tablet, capsule, aqueous or oily solution or suspension, or emulsion, or in the form of a sterile solution or suspension suitable for parenteral administration, or in the form of an ointment or lotion for topical administration, or in the form of a suppository.

5. A method for producing an antiandrogenic effect in a warm-blooded animal which comprises administering to said animal an effective amount of a compound claimed in claim 1.

* * * * *